(12) United States Patent
Diamond et al.

(10) Patent No.: US 9,408,680 B2
(45) Date of Patent: Aug. 9, 2016

(54) DRIVE SYSTEM

(75) Inventors: David Diamond, Dublin (IE); Jean Diamond, Dublin (IE)

(73) Assignee: Jean Diamond, Dublin (IE)

( * ) Notice: Subject to any disclaimer, the term of this patent is extended or adjusted under 35 U.S.C. 154(b) by 0 days.

(21) Appl. No.: 13/697,153

(22) PCT Filed: May 16, 2011

(86) PCT No.: PCT/EP2011/057849
§ 371 (c)(1),
(2), (4) Date: Nov. 9, 2012

(87) PCT Pub. No.: WO2011/141577
PCT Pub. Date: Nov. 17, 2011

(65) Prior Publication Data
US 2013/0055515 A1  Mar. 7, 2013

(30) Foreign Application Priority Data

May 14, 2010 (IE) .................................. S2010/0314
Sep. 7, 2010 (IE) .................................. S2010/0555

(51) Int. Cl.
*A61C 17/26* (2006.01)
*A46B 13/02* (2006.01)
*A46B 9/04* (2006.01)

(52) U.S. Cl.
CPC . *A61C 17/26* (2013.01); *A46B 9/04* (2013.01); *A46B 13/02* (2013.01); *Y10T 74/1836* (2015.01)

(58) Field of Classification Search
USPC ................. 15/22.1, 22.2, 22.4, 23, 28; 74/63; 173/47, 164, 213, 215–217
See application file for complete search history.

(56) References Cited

U.S. PATENT DOCUMENTS

| | | | | |
|---|---|---|---|---|
| 3,066,337 A | * | 12/1962 | Caro ............................... | 15/22.1 |
| 3,168,834 A | * | 2/1965 | Smithson ......................... | 74/23 |
| 3,379,906 A | * | 4/1968 | Spohr ............................. | 310/50 |
| 3,489,936 A | * | 1/1970 | Boyles ............................ | 310/47 |
| 3,524,088 A | * | 8/1970 | Ryckman, Jr. .................. | 310/50 |
| 3,546,501 A | * | 12/1970 | Kircher .......................... | 310/50 |
| 3,848,336 A | | 11/1974 | Copeland | |
| 4,274,173 A | * | 6/1981 | Cohen .............................. | 15/28 |
| 4,326,314 A | * | 4/1982 | Moret et al. .................... | 15/22.1 |
| 4,397,055 A | * | 8/1983 | Cuchiara ........................ | 15/22.1 |
| 4,432,729 A | * | 2/1984 | Fattaleh ........................ | 433/118 |

(Continued)

FOREIGN PATENT DOCUMENTS

| | | | |
|---|---|---|---|
| DE | 3544256 | * | 6/1987 |
| GB | 2005999 | * | 5/1979 |

(Continued)

OTHER PUBLICATIONS

International Search Report and Written Opinion of the International Searching Authority from corresponding International (PCT) Application No. PCT/EP2011/057849, mailed Aug. 17, 2011.

*Primary Examiner* — Mark Spisich
(74) *Attorney, Agent, or Firm* — Gardner, Linn, Burkhart & Flory, LLP (57) ABSTRACT

The present invention provides a drive system having particular utility in an electric toothbrush, the drive system comprising a coupling (14) which is connectable between a drive source (12) and a brush head (16), the coupling being adapted to impart first and second independent brushing motions to the head.

21 Claims, 10 Drawing Sheets

(56) References Cited

U.S. PATENT DOCUMENTS

| | | | |
|---|---|---|---|
| 4,522,503 A | 6/1985 | Salter | |
| 4,710,995 A * | 12/1987 | Joyashiki et al. | 15/22.1 |
| 4,756,202 A * | 7/1988 | Kawamoto | 74/23 |
| 5,173,983 A | 12/1992 | Le | |
| 5,442,827 A * | 8/1995 | Hommann | 15/22.1 |
| 5,495,632 A | 3/1996 | Baker | |
| 5,504,959 A * | 4/1996 | Yukawa et al. | 15/22.1 |
| 7,156,108 B2 * | 1/2007 | Xin | 132/322 |
| 7,156,187 B1 * | 1/2007 | Townsan | 173/1 |
| 7,464,430 B2 * | 12/2008 | Filsouf | 15/22.1 |
| 8,448,281 B2 * | 5/2013 | Heatley-Adams et al. | 15/22.1 |
| 8,516,641 B2 * | 8/2013 | Diamond et al. | 15/22.1 |
| 2005/0088911 A1 | 4/2005 | Sordelli et al. | |
| 2007/0189116 A1 | 8/2007 | Wang | |
| 2010/0132140 A1 | 6/2010 | Diamond | |
| 2010/0282096 A1 * | 11/2010 | Fletcher | 99/421 A |

FOREIGN PATENT DOCUMENTS

| | | | |
|---|---|---|---|
| JP | 5-137615 | * | 6/1993 |
| JP | 5-137616 | * | 6/1993 |
| JP | 5-199918 | * | 8/1993 |
| JP | 7-213342 | * | 8/1995 |
| WO | 97/28757 | * | 8/1997 |
| WO | 2008/125269 | * | 10/2008 |

* cited by examiner

DRIVE SYSTEM

FIELD OF THE INVENTION

This invention relates to a drive system, and in particular a drive system which is adapted to provide simultaneous and/or sequential drive in two separate directions, for example to a brush head or the like, in particular as part of a handheld electric toothbrush, and which facilitates the ready replacement of various components of the drive system and/or brush head by the end user.

BACKGROUND OF THE INVENTION

It is often desirable, when using tools such as brushes or the like, to mechanise the operation of same, both from a labour saving point of view, and often to improve the performance of such tools by increasing the speed or optimising a particular movement of same. Such is the case, for example, with an electric toothbrush, mixer, polishers/buffer or the like. However, in mechanising the operation of such tools, it is often necessary to limit the type of movement that the tool or tool head can undergo, in particular to keep the overall size, weight and complexity of the device within reason, in order to be practical for everyday use as a handheld and self contained tool. This is particularly evident in the field of electric toothbrushes, which can provide improved cleaning capabilities, but usually have a relatively limited range of movement at the brush head, in order to satisfy the above mentioned criteria.

The applicants International patent application WO2008/125269 discloses a toothbrush, in particular a mechanical toothbrush more commonly known as an electric toothbrush, which includes a spherical brush head which is capable of undergoing at least first and second independent brushing motions in order to improve the overall brushing effectiveness.

A number of embodiments are disclosed which detail various methods of delivering the first and second independent brushing motions to the head, and which incorporate different drive mechanisms to transmit motion to the bristled head of the brush. However, as with any toothbrush, whether mechanically/electrically or manually operated, the bristle on the head will in time become worn or significantly deformed to the point of requiring replacement. In order to prolong the working life of the head, and in particular the drive mechanism, it is preferable if the drive mechanism can be substantially sealed from the ingress of water and other contaminants such as toothpaste, while optionally including and retaining a lubricant about the drive mechanism. In addition, for a product such as an electric toothbrush it is important that the head of the brush can be replaced, while retaining the body, which includes the motor, control circuitry, and other aspects of the brush. It is also important that the head can be replaced quickly and easily by the end user. In addition to providing for the quick and easy replacement of the head by the user, there are other issues to be addressed in designing and manufacturing an electric toothbrush. In particular the cost and complexity of manufacture must be kept relatively low in order to provide an economically viable product, for example by designing the product for convenience of assembly during production. As the toothbrush of WO2008/125269 has a more complex drive mechanism than a conventional electric toothbrush, these are greater challenges to overcome.

It is therefore an object of the present invention to overcome some of the above-mentioned problems of the prior art.

SUMMARY OF THE INVENTION

According to a first aspect of the present invention there is provided A drive system for connection to a drive source, the drive system comprising a head; and a coupling connectable between the drive source and the head and operable to impart at least first and second independent motions to the head.

Preferably, the coupling is operable to impart continuous rotary motion to the head for both the first and the second motions.

Preferably, the coupling is adapted to rotate the head about a first axis as the first motion and independently and/or simultaneously about a second axis as the second motion.

Preferably, the first and second axes are substantially orthogonal to one another.

Preferably, the first and second axes pass through the centre of the head.

Preferably, the coupling comprises a first pulley and a second pulley, and a belt extending between the first and second pulleys, the first pulley arranged to be driven by the drive source and the second pulley arranged to drive the head.

Preferably, the coupling comprises an elongate rigid support extending between the first and second pulleys and at a free end of which support the head is mounted.

Preferably, the belt extends substantially longitudinally of the support.

Preferably, the support is rotatable by the drive source about a longitudinal axis of the support.

Preferably, the support forms a guide for the belt.

Preferably, the head comprises a rotatable element to which the coupling is arranged to impart the first and second independent motions.

Preferably, the second pulley is formed integrally with the rotatable element.

Preferably, the belt comprises a toothed belt.

Preferably, the free end of the support comprises a tab having an aperture therein through which two halves of the rotatable element are secured to one another.

Preferably, the tab comprises a ring and each half of the rotatable element forms a seal with the ring when secured thereto.

Preferably, the head comprises an array of bristles extending outwardly from the rotatable element.

Preferably, the bristles are provided on each half of the rotatable element and are oriented, at or adjacent an interface between the halves, to converge in order to provide continuity to a cleaning surface defined by the bristles.

Preferably, the drive system comprises the drive source, and wherein the drive source comprises a pair of concentric drive shafts, a first shaft arranged to drive the first pulley, and a second shaft arranged to effect rotation of the support.

Preferably, the drive source comprises a clutch displaceable between an engaged and a disengaged state, in the engaged state enabling synchronous rotation of the first and second shafts, and in the disengaged state enabling independent rotation of the first shaft.

Preferably, the drive system comprises a sleeve surrounding at least a portion of the support and within which sleeve the support is rotatable about a longitudinal axis of the sleeve.

Preferably, the coupling is releasably engageable with the drive source.

According to a second aspect of the present invention there is provided a handheld device comprising a drive system according to the first aspect of the invention, and a body housing the drive source; wherein the drive system is releasably mountable to the body in operative engagement with the drive source.

Preferably, the device comprises a transducer disposed internally of the body and operable to transfer drive from the drive source to the first pulley and to effect rotation of the support relative to the body.

Preferably, the transducer is rotatable within the body by the drive source in order to impart the second independent motion.

Preferably, the drive system is insertable into the body and engagable with the transducer by means of the longitudinal insertion of a free end of the coupling into the body.

DETAILED DESCRIPTION OF THE DRAWINGS

Referring now to FIGS. 1 to 4 of the accompanying drawings there is illustrated a first embodiment of a drive system according to the present invention, generally indicated as 10, which is operable to impart first and second independent motions, preferably continuous rotation, to a rotatable element of the drive system, and which may therefore find utility in an electric toothbrush or the like. It will however be appreciated that alternative uses of the drive system 10 may be employed, for example for use as a polisher, a grinder, a drill, a mixer/agitator or any other suitable application.

Figure 1:
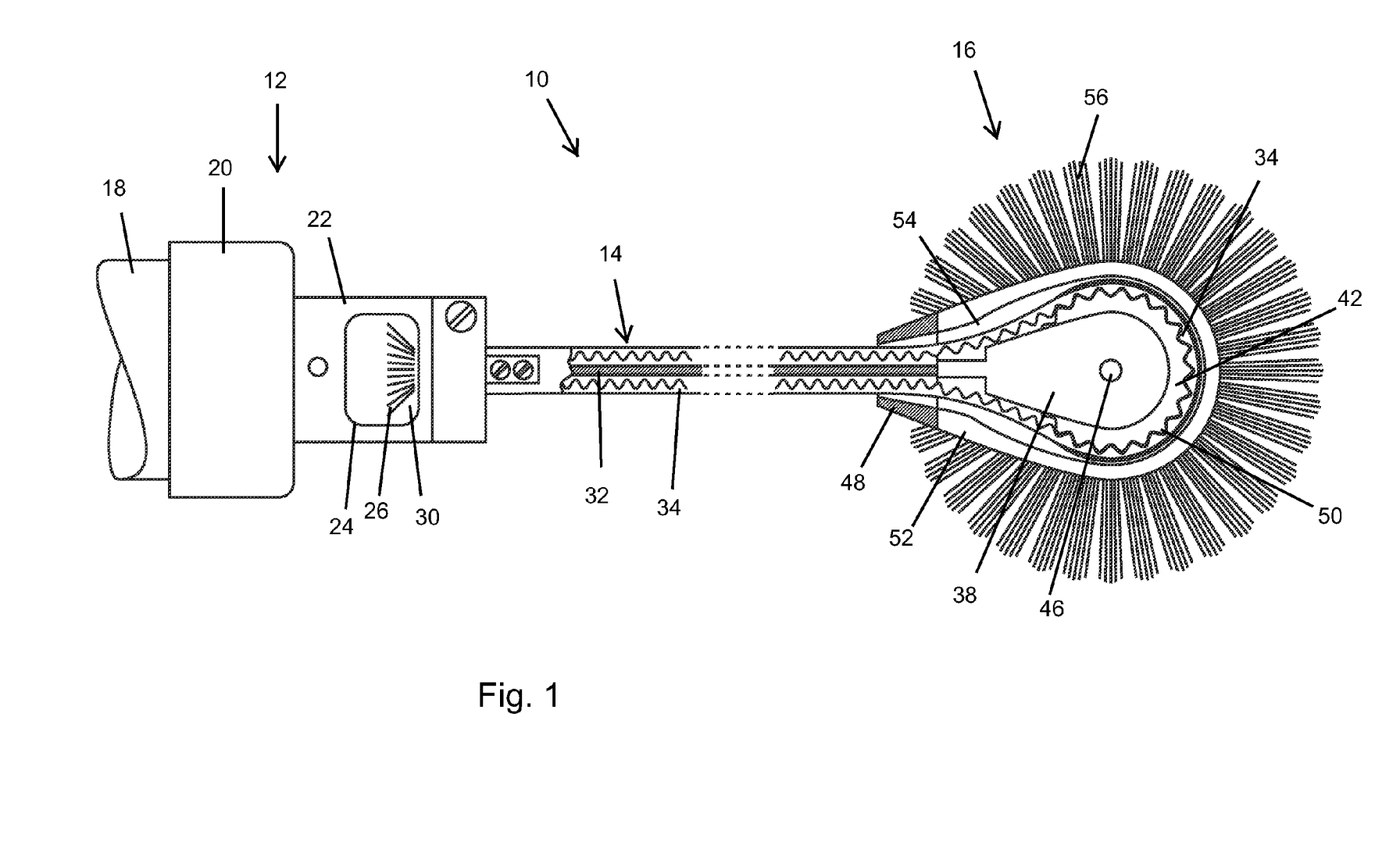
FIG. 1 illustrates a sectioned side view of a drive system according to an embodiment of the present invention.

The drive system 10 is connectible with, and optionally comprises, a drive source 12 which may comprise or be connectable with an electric/hydraulic/mechanical drive means as will be described hereinafter in order to provide the motive power to the drive system 10. The system 10 further comprises a coupling 14 extending between the drive source 12, and a head 16 mounted at the opposed end of the coupling 14. The head 16 defines the working end of the drive system 10, as will be described in detail hereinafter, and may for example comprise a brush head having an array of bristles thereon, in order to for example to effect cleaning/scrubbing or the like.

Returning to the drive source 12, there is comprised a motor 18 which in the present embodiment is in the form of an electric motor which is arranged to drive, via a clutch 20, a transducer in the form of a gear housing 22. Extending between the clutch 20 and the gear housing 22 are concentric first and second shafts (not shown). The first shaft projects into a window 24 in the gear housing 22 and has a first bevel gear 26 mounted on the free end thereof. This first bevel gear 26 meshes with a second bevel gear 30 secured to the exterior of the gear housing 22. Mounting co-axially with the second bevelled gear 30, on the interior of the gear housing 22, is a first pulley or cog in the form of a toothed pinion (not visible in the drawings), which is therefore directly driven by the second bevel gear 30.

Extending from the gear housing 22, and forming part of the coupling 14, is a support 32 in the form of a rigid shaft at the opposed free end at which is mounted the head 16. The coupling 14 further comprises an endless belt 34 which passes around the first pulley/gear pinion (not shown) within the gear housing 22, and exits the gear housing 22 to extend along the support 32 and into the head 16, before returning from the head 16 back along the support 32 to re-enter the gear housing 22. In the embodiment illustrated the support 32 defines a pair of recessed channels 36 therein which are shaped and dimensioned to house the belt 34. Returning to the drive source 12, there is comprised a motor 18 which in the present embodiment is in the form of an electric motor which is arranged to drive, via a clutch 20, a transducer in the form of a gear housing 22. Extending between the clutch 20 and the gear housing 22 are concentric first and second shafts (not shown). The first shaft projects into a window 24 in the gear housing 22 and has a first bevel gear 26 mounted on the free end thereof. This first bevel gear 26 meshes with a second bevel gear 30 secured to the exterior of the gear housing 22. Mounting co-axially with the second bevelled gear 30, on the interior of the gear housing 22, is a first pulley or cog in the form of a toothed pinion (not visible in the drawings), which is therefore directly driven by the second bevel gear 30.

Figure 2:
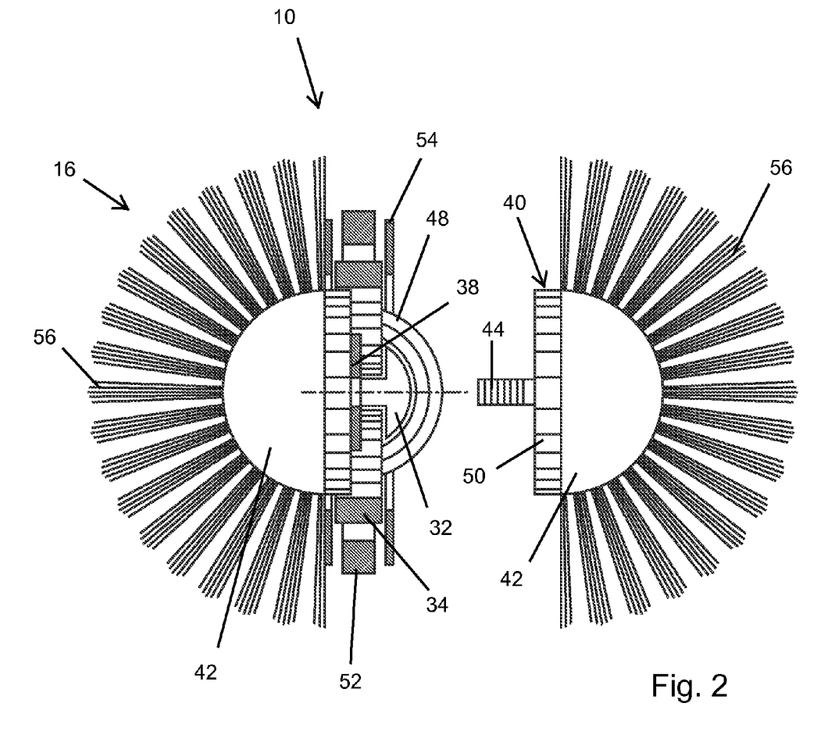
FIG. 2 illustrates an exploded end view of a head of the drive system illustrated in FIG. 1.
Figure 3:
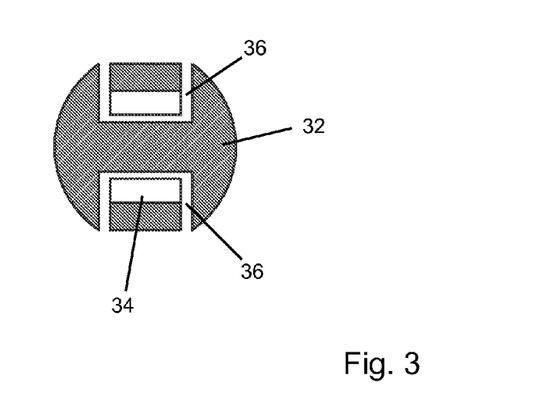
FIG. 3 illustrates a sectioned view of a support forming part of the drive system illustrated in FIGS. 1 and 2.

Turning then to the head 16, the support 32 extends to form a tab 38 at the free end thereof, which in use is located at the interior of the head 16, and forms the main mounting and bearing by which the head 16 is secured to the drive system 10. The head 16 further comprises a rotatable element 40, which in the embodiment illustrated is substantially spherical, and is comprised of a pair of hemispherical halves 42 which are secured to one another through the tab 38, via a spindle 44. The spindle 44 in the embodiment illustrated is permanently fixed into one of the halves 42, and the exposed portion of the spindle 44 is threaded for engaging with the opposed half 42 as shown in FIG. 2. The spindle 44 passes through a central aperture 46 in the tab 38, and is then threaded into the opposed half 42. Thus the rotatable element 40, in use, is spherical in shape and rotatably mounted on the tab 38.

As the belt 34 reaches the head 16 it passes through a collar 48 which circumscribes both the support 32 and the two sides of the belt 34 housed in the channels 36, before the belt 34 separates outwardly to pass around an exterior surface of the rotatable element 40. The rotatable element 40 thus acts as a second pulley/gear pinion around which the belt 34 passes, thereby enabling the belt 34 to impart motion in the form of continuous rotation to the rotatable element 40. This rotation comprises a first independent motion in the form of continuous rotation about a first axis defined by the spindle 44.

In order to improve the transfer of power from the belt 34 to the rotatable element 40, in particular when the rotatable element 40 is under load, it is preferable that the belt 34 comprises a toothed belt and, although not illustrated, the belt 34 may have various cross sections such as a conventional V-belt profile or the like. The rotatable element 40 is thus provided with a corresponding circumferential array of teeth 50 formed integrally within an outer surface of the two halves 42 of the rotatable element 40. A portion of the teeth 50 are formed in each half 42 of the rotatable element 40 and adjacent the contacting faces of the halves 42. The teeth 50 thus define a track or second pulley on the surface of the rotatable element 40 around which the belt 34 passes.

In order to prevent slippage of the belt 34 over the teeth 50, the head 16 preferably comprises a guide 52, which extends from the collar 48 and circumscribes the belt 34, thus maintaining the belt 34 in driving engagement with the teeth 50. The belt 34 may be formed from any suitable material, and is preferably formed in conventional fashion from fibre reinforced rubber, providing both the necessary strength, and relatively quiet operation, which is desirable when the system 10 is to be used in applications such as an electric toothbrush. In use it is likely that the support 32 and the sections of the belt 34 located in the channels 36 would be surrounding by a protective covering such as a plastic sleeve or the like.

In the embodiment illustrated the head 16 is also preferably provided with a pair of guards 54, one located on either side of the belt 34 and circumscribing the respective hemisphere half 42. Each guard 54 is positioned in close proximity to the interface between the belt 34 and the teeth 50 in order to prevent the ingress of any item to the interface, which could become entangled with the belt 34 and/or cause damage or slippage over the teeth 50. For example in the embodiment illustrated the rotatable element 40 is in the form of a brush head and is provided with an array of bristles 56 thereon, in order to effect a brushing action to allow the drive system 10 to function as an electric toothbrush. The guards 54 thus ensure that, in particular during use, the bristles 56 do not become entrained between the belt 34 and the teeth 50. Each of the guards 54 is secured to the collar 48, although it will be appreciated that any other means of mounting the guards 54 to the head 16 may be employed.

Thus as described above the belt 34 is used to impart a first independent driving motion to the head 16, and in particular the rotatable element 40. This first independent driving motion is continuous rotation, in either direction, about the axis defined by the spindle 44. However the drive system 10 is adapted to impart a second independent motion to the head 16, and again in particular the rotatable element 40. The first motion is achieved by driving the first shaft (not shown), which in turn effects driving of the belt 34 via the bevel gears 26, 30. However, the clutch 20 is operable to effect a synchronous driving of the first and second shafts. This results in the gear housing 22 being rotated about an axis defined by a longitudinally axis of the support 32. This rotation of the gear housing 22 thus effects rotation of both the support 32 connected thereto, and as a result rotation of the head 16 connected to the support 32. This gives rise to a second independent motion, in the form of a rotational motion, and preferably a continuous rotational motion about an axis defined by a longitudinal axis of the support 32. By driving the first and second shafts (not shown) synchronously, the first bevel gear 26 will remain stationary relative to the second bevel gear 30 which is also rotating at the same speed as a result of the rotation of the gear housing 22. This ensures that as the second brushing motion is being implemented the belt 34 remains stationary, thus ensuring that the first brushing motion remains independent of the second brushing motion. It should however be understood that the first and second motions imparted to the rotatable element 40 could be applied simultaneously, by rotating the housing 22 and driving the belt 34 at the same time to achieve variable patterns of movement at the head 16.

It should however be understood that there are various means by which the two above mentioned independent motions may be achieved. For example, rather than having two concentric shafts extending from the clutch 20 into the gear housing 22, a single shaft (not shown) could be used, which would extend from the clutch 20 into the gear housing 22 and be connected to the first bevel gear 26. The clutch 20 is then adapted to selectively lock the gear housing 22 relative to the clutch 20, or to release it for rotation relative thereto. This locking/releasing may be achieved by any suitable means, for example a switch actuated mechanical lock (not shown) which can slide out of the clutch 20 to engage and lock the gear housing 22, and which can then be retracted in order to release the gear housing 22. In order to impart the first motion to the head 16 the gear housing 22 is locked to the clutch 20. As a result when the single shaft extending from the clutch 20 to the first bevel gear 26 is driven the gear housing 22 cannot move and so the drive is transmitted directly to the first bevel gear 26. With this single shaft arrangement a bearing (not shown) or the like is provided between the shaft and the gear housing 22 in order to allow the shaft to turn freely despite the gear housing 22 being locked in place. As described above this will result in the belt 34 being driven in order to impart the first brushing motion to the head 16. To impart the second independent motion to the head 16 the gear housing 22 is disengaged or unlocked from the clutch 20, for example as described above by releasing the switch actuated mechanical lock. As a result when the single shaft is driven the entire gear housing 22, and thus the coupling 14, will rotate to impart the second independent motion to the head 16. The bevel gear 26 is not turned within the gear housing 22 as the drive from the shaft will take the path of least resistance to the head 16, which is through rotation of the entire gear housing 22 which presents less resistance than driving the belt 34.

Referring now to FIGS. 4 to 9 there is illustrated a second embodiment of a drive system according to the present invention, generally indicated as 110, again for use in a hand held device such as an electric toothbrush or the like. In this second embodiment like components have been accorded like reference numerals, and unless otherwise stated, perform a like function. The system 110 is adapted, as with the first embodiment, to impart first and second independent motions to a head 116 of the toothbrush. It will of course be appreciated that the head 116 may be substituted by any other suitable attachment if the system 110 is to be employed in a device other than an electric toothbrush.

Figure 4:
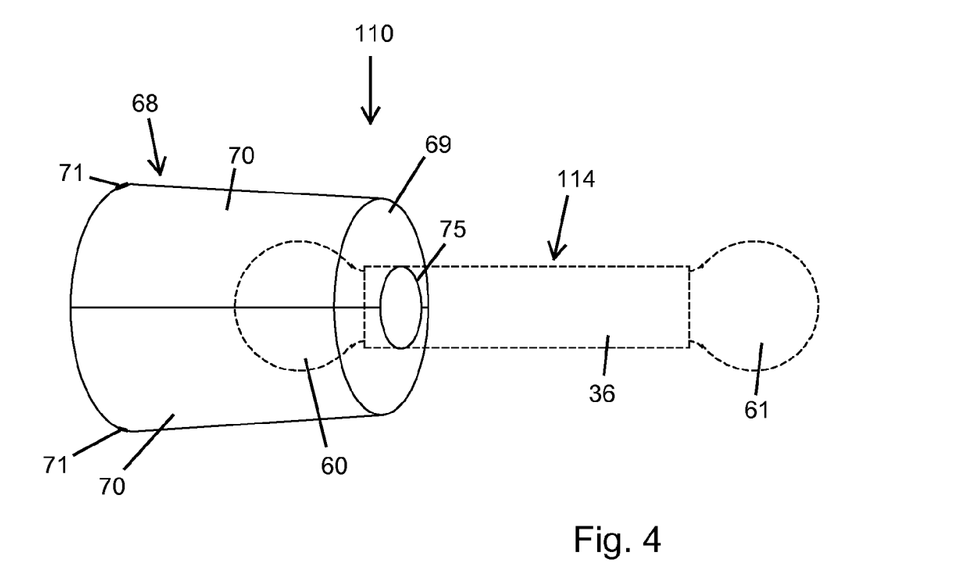
FIG. 4 illustrates a perspective view of a head of an electric toothbrush according to an alternative embodiment of the present invention.

The head 116, in the second embodiment, is again substantially spherical and although not illustrated is covered in its entirety by outwardly extending bristles (not shown). The detailed operation of the system 110, as a component part of a toothbrush or the like, will be described once the configuration and operation of the drive system 110 has been explained.

Thus referring in particular to FIGS. 6 to 9 the drive system 110 comprises a coupling 114 in the form of a hollow casing 114 comprising first and second free ends 60, 61 connected by a support in the form of a hollow central portion 132 extending therebetween. It can be seen from FIGS. 7 and 8 that the first and second ends 60, 61 are circular in profile while the central portion 132 is substantially elongate. From FIG. 9 it can be seen that the entire casing 114 is of a uniform thickness and is relatively narrow. For example if used in an electric toothbrush the casing 114 may be less than 5 mm in thickness.

The casing 114 may be formed from any suitable material and in any suitable manner, and for example is preferably moulded from a plastic material or the like.

Figure 7:
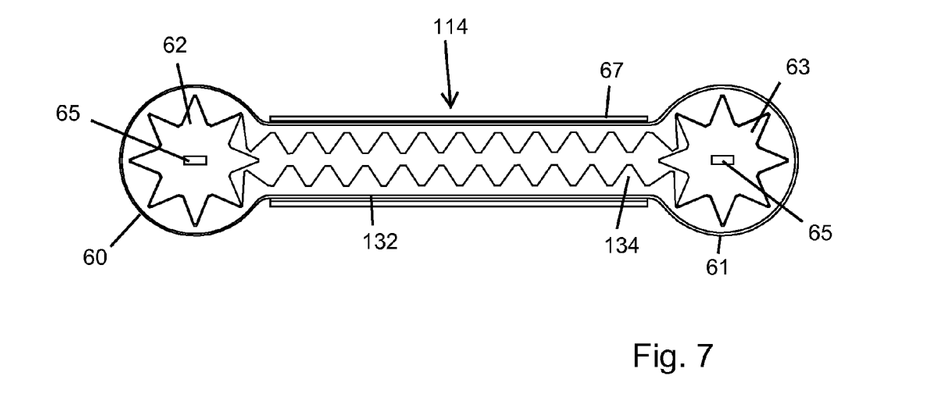
FIG. 7 illustrates a sectioned side view of the coupling shown in FIG. 6, housing a drive mechanism.
Figure 8:
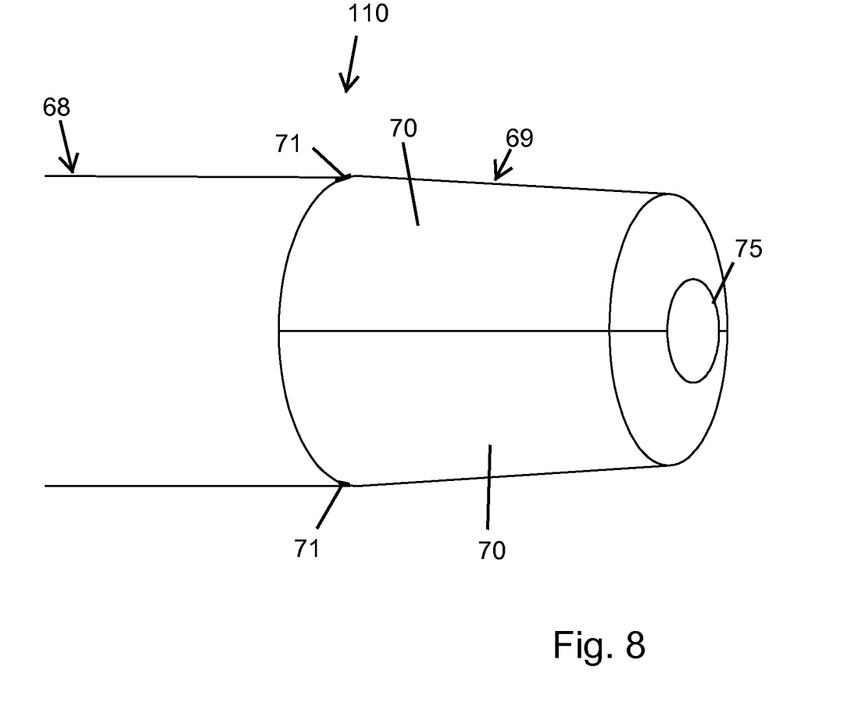
FIG. 8 illustrates a perspective view of the head of the toothbrush of FIGS. 4 to 7 in the absence of the coupling.
Figure 9:
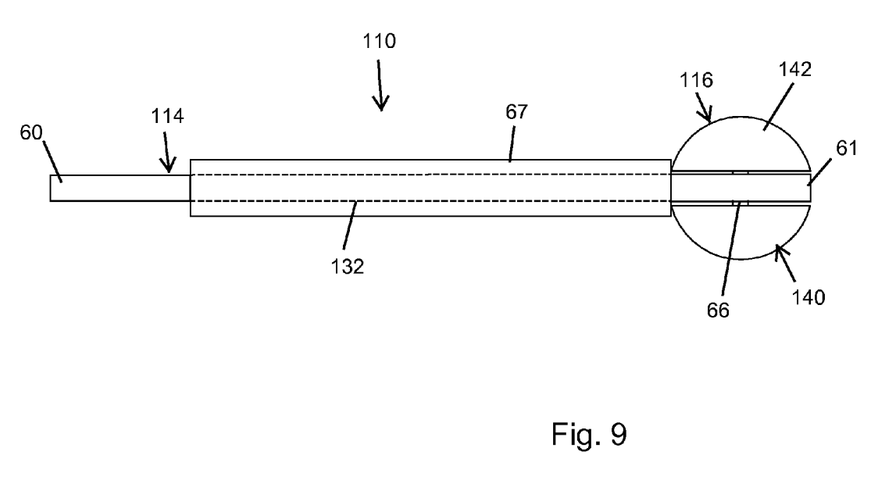
FIG. 9 illustrates a plan view of the coupling illustrated in FIGS. 6 and 7 with a spherical brush head secured at one end thereof.

Referring to FIG. 7 the system 110 is shown in section. Located within the casing 114 is a drive assembly comprising a first toothed pulley or pinion 62 seated in the first end 60 and a second toothed pulley or pinion 63 seated in the second end 61. Extending between and around each of the pulleys 62, 63 is a toothed belt 134 which forms part of the drive assembly and is preferably formed from a material such as reinforced rubber or the like. An aperture 64 in either end 60, 61 of the casing 114 facilitates external access to a corresponding aperture 65 in each of the pulleys 62, 63. Thus it will be appreciated that if the first pulley 62 is rotated from the exterior, for example by means of a drive shaft passed through the aperture 64 in the casing 114, this rotation will be transmitted by the belt 134 to the second pulley 63. This drive can then be transmitted to the head 116 which may be secured to the second pulley 63 via an axle 66 passing outwardly through the apertures 65 on the casing 114 at the second end 61. The belt 134 is preferably narrow in width, for example 1 to 2 mm in width, in order to facilitate the narrow width of the casing 114. It is preferable, as the belt 134 will undergo wear during use, that the transition between both the first and second ends 60, 61 and the central portion 132, on the interior of the casing 114, is curved in order to minimise wear on the belt 134 at these points. It is also envisaged that a lubricant or the like may be provided on the interior of the casing 114 in order to minimise wear of the belt 134 and generally improve the operation thereof. However, as described in more detail below, the casing 114, with the head 116 mounted thereon, is designed to be user replaceable, in order to allow a new casing 114 and head 116 to be fitted to a toothbrush once the original head 116 becomes worn, or in the event of damage such as a break in the belt 134.

The system 110 further comprises a sleeve 67 located co-axially about the central portion 132 of the casing 114. The sleeve 67 is cylindrical in form and is dimensioned to permit the casing 114 to rotate within the sleeve 67 about a longitudinal axis thereof. To this end bearings or bushings (not shown) may be provided between the sleeve 67 and the exterior of the casing 114. The sleeve 67 may therefore be held immobile while the casing 114 can be rotated therein. Again the sleeve 67 may be formed from any suitable material, preferably a plastic.

Returning now in particular to FIGS. 4 and 5 the operation of the drive system 110 in combination with the electric toothbrush will be described in detail. Thus the toothbrush comprises a relatively conventional body 68, which will house a drive source (not shown) in the form of an electric motor or the like. The body 68 will also include a compartment or space for a power source such as a battery, although equally the toothbrush could be mains powered. Similarly control circuitry or the like will be housed within the body 68. As with a conventional electric toothbrush, as well as housing all of the above components, the body 68 serves as a handle by which the toothbrush may be held and manipulated.

Figure 5:
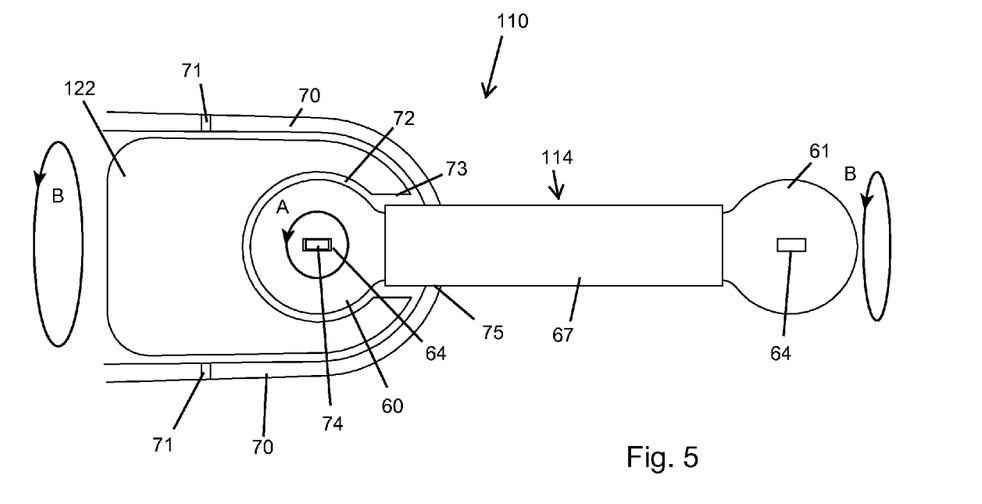
FIG. 5 illustrates a sectioned view of the head of the toothbrush as shown in FIG. 4.
Figure 6:
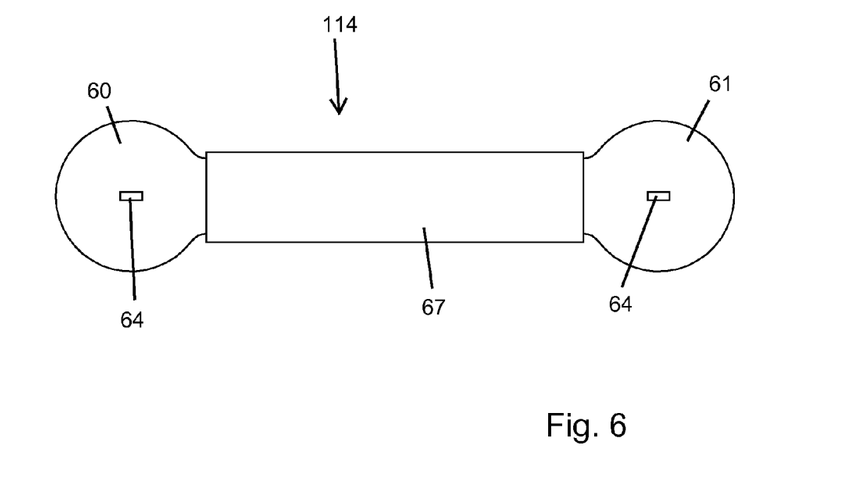
FIG. 6 illustrates a side view of a coupling for use with the toothbrush illustrated in FIGS. 4 and 5.

The body 68 further comprises a nose 69 defined by a pair of hinged access panels 70 each of which is mounted on a hinge 71 in order to allow one or both of the panels 70 to be hinged outwardly in a clam shell arrangement. The panels 70 may be hinged between open and closed positions by the user, in order to expose or conceal the interior of the toothbrush. Located within the interior space defined by the pair of panels 70 is a transducer 122 which is operable, as will be described hereinafter, to transmit to the head 116, via the casing 114, first and second independent motions in similar fashion to the transducer of the first embodiment. The transducer 122 defines a substantially circular recess 72 which is shaped and dimensioned to receive the first end 60 of the casing 114 therein. The recess 72 has a narrow or restricted neck 73 which will prevent the axial withdrawal of the first end 60 from the recess 72 once positioned therein. It should also be appreciated that some form of releasable locking mechanism (not shown) could be provided to further secure the first end 60 of the casing 114 within the recess 72.

The transducer 122 comprises a drive shaft 74 projecting upwardly into the recess 72, which drive shaft 74 is located and dimensioned to pass through the aperture 64 in the first end 60 in order to engage with the first pulley 62. The drive shaft 74 can be driven by the electric motor (not shown) in order to rotate in the direction indicated by arrow A, which gives rise to the first independent brushing motion. Controls (not shown) for the toothbrush may also be used to reverse the direction of rotation of the drive shaft 74. The electric motor is also operable to effect rotation of the entire transducer 122 within the nose 69 about an axis corresponding with a longitudinal access of the sleeve 67 when the system 110 is mounted to the toothbrush, in a direction indicated by the arrow B. This gives rise to the second independent brushing motion. Again controls (not shown) for the toothbrush may be used to reverse the direction of rotation of the transducer 122.

Turning then to the operation of the toothbrush, the access panels 70 are initially hinged into the open position in order to provide access to the transducer 122. The casing 114, with the head 116 secured at the second end 61, is then seated with the first end 60 located within the recess 72 of the transducer 122. This results in the drive shaft 74 being seated into the aperture 64 in the first end 60 and thus engaging the first pulley 62. The access panels 70 are then hinged back into the closed position with an opening 75 defined between the interface of the panels 70 accommodating the sleeve 67. The opening 75 is dimensioned to grip the exterior of the sleeve 67 when the panels 70 are in the closed position, in order to immobilise the sleeve 67 with respect to the body 68 of the toothbrush. To this end the opening 75 may be provided with a lip or the like in order to increase the surface area in contact with the sleeve 67. Similarly the opening 75 could be lined with a material such as rubber or the like in order to increase the friction between the opening 75 and the exterior of the sleeve 67, while also providing a seal to the ingress of moisture or the like to the body 68. Alternatively the sleeve 67, at the point at which the opening 75 engages same, could be provided with indentations while the opening 75 is provided with corresponding projections or teeth to engage the indentations. Locking means (not shown) may be provided in order to lock the access panels 70 in the closed position. Such locking means could take the form of mechanical, electrical or magnetic looking means. Once the access panels 70 have been hinged back into the closed position the system 110 is secured in place as an integral part of the toothbrush. The toothbrush is then ready for operation by the end user.

Controls (not shown) on the toothbrush may then be used to drive the transducer 122 as described above. By operating the drive shaft 74 without rotating the transducer 122 the first pulley 62 will be driven, thereby driving the second pulley 63 via the belt 134. This will drive the bristled head 116 as a first independent motion in the form of rotary motion about a first axis corresponding with the axle 66. In order to effect the second independent motion, through operation of the toothbrush controls (not shown), the entire transducer 122 is rotated in the direction of arrow B by the electric motor. As the sleeve 67 is immobilised by the access panels 70, the casing 114 will then rotate within the sleeve 67 about a longitudinal axis of the sleeve 67. This will thus impart a second independent motion to the head 116 around a second axis corresponding to a longitudinal access of the sleeve 67. In the embodiment illustrated the shaft 74 is driven from the electric motor through a set of bevel gears (not shown) located at the rear of the transducer 122 as seen in FIG. 5. Thus during rotation of the transducer 122 to achieve the second independent motion, it is necessary to simultaneously drive the shaft 74 at a speed which will ensure that the bevel gear (not shown) on the shaft 74 keeps pace with the rotation of the bevel gear (not shown) connected to the electric motor, thereby ensuring that relative to one another there is no movement between the two bevel gears and no motion will be imparted to the first pulley 62. As a result the head 116 will rotate about the longitudinal axis of the casing 114 without rotating about the axle 66.

It should be understood that the sleeve 67 is not an essential element of the invention, and could be omitted while maintaining the above functionality. However, the rotating casing 114 would then be exposed, and may cause discomfort to the user, as the rotating casing 114 would contact the users' lips and/or teeth during operation of the toothbrush. The sleeve 67 is preferably a user replaceable element of the system 110, preferably in combination with the casing 114.

It should also be appreciated that the drive assembly as defined by the first and second pulleys 62, 63 and the belt 134 could be replaced with any other suitable alternative. For example, the first and second pulleys 62, 63 could be replaced with first and second bevelled gears, with a shaft extending longitudinally through the central portion 132 between the gears. A suitable bevelled gear could be provided on either end of the shaft in order to mesh with the first and second gears. It is envisaged, in particular when the system 110 is used with an electric toothbrush, that the head 116 will be permanently secured to the casing 114 and thus not removable by the end user. It is preferably that the combined casing 114, including the internal drive assembly, and the head 116 be replaced as a single unit.

Referring now to FIGS. 10 to 14 there is illustrated a further alternative embodiment of a drive system according to the present invention, generally indicated as 210, for use with an electric toothbrush (not shown) or the like. In this embodiment like components have again been accorded like reference numerals, and unless otherwise stated perform a like function. The system 210 comprises a coupling 214, which is operable, in use, to impart first and second independent motions to a head 216, which in the embodiment illustrated is in the form of a bristled head for use as an electric toothbrush. The coupling 214, as with the previous embodiment, is adapted to be releasably engaged with the toothbrush in order to enable user replacement of the coupling 214 and brush head 216, for example when the bristles become worn.

Figures 11, 12:
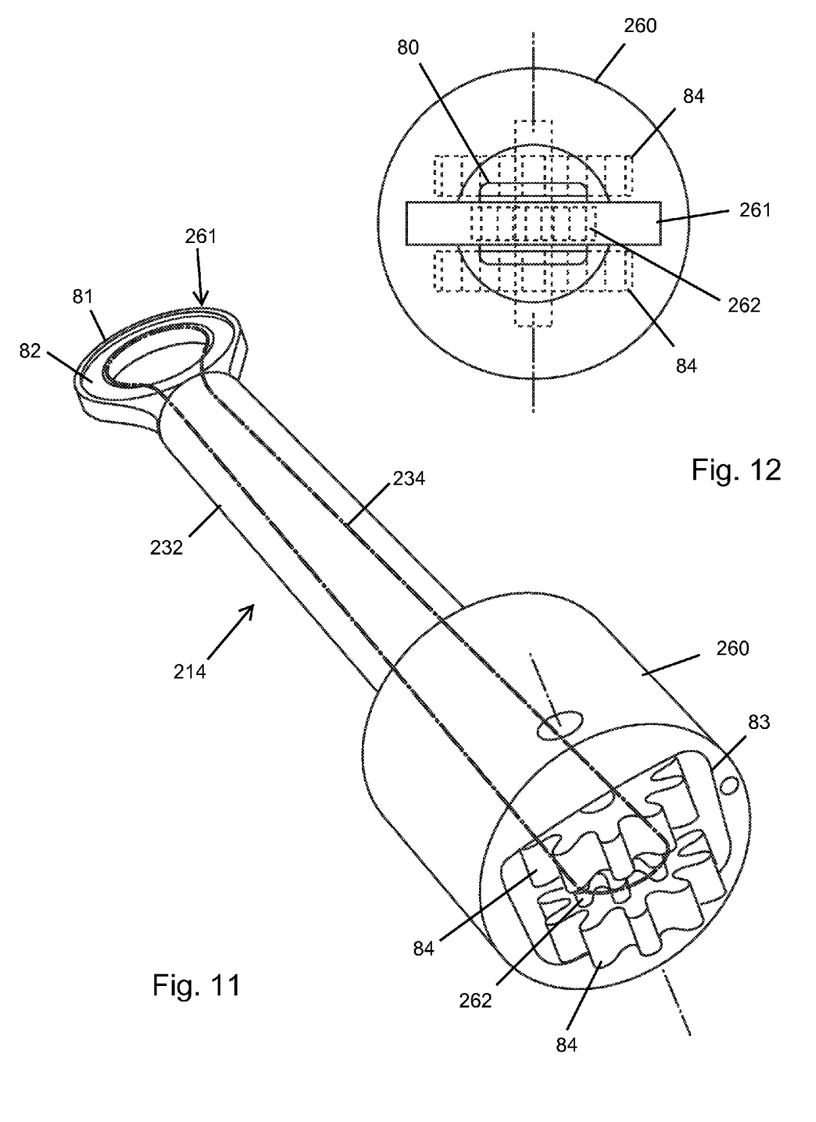
FIG. 11 illustrates a perspective view of a replaceable coupling of the toothbrush shown in FIG. 10.
FIG. 12 illustrates a plan view of the coupling shown in FIG. 11.
Figure 13:
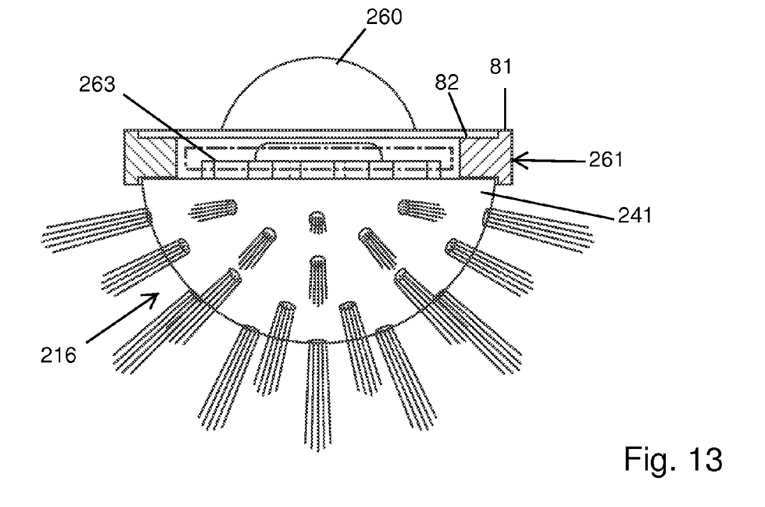
FIG. 13 illustrates an end view of a head of the toothbrush shown in FIG. 10.

The coupling 214 comprises a first end 260 which in use permits drive to be transferred from the main body of the toothbrush to the coupling 214, and therefore on to head 216. The coupling 214 further comprises an opposed second end 261, which comprises a tab in the form of an open ring 261 into which, in use, two hemispherical halves 241 of the head 216 are seated and retained. Extending between the first and second ends 260, 261 is a support in the form of a hollow cylindrical tube 232, which in the embodiment illustrated is moulded, along with the first and second ends 260, 261, as a single unit. Passing through the hollow tube 232 is a toothed belt 234 (shown schematically by a dashed line), which is engaged about first and second pulleys 262, 263, located, respectively, in the first and second free ends 260, 261.

Figure 14:
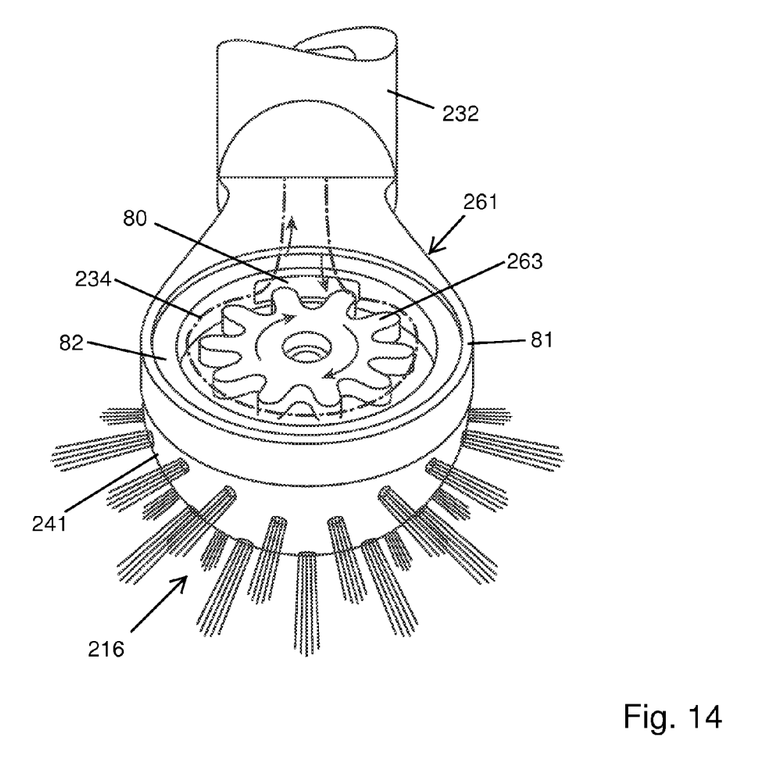
FIG. 14 illustrates a perspective view of the head as shown in FIG. 13.

Referring to the second end 261, as most clearly shown in FIG. 14, the belt 234 exits the hollow tube 232 via a narrow opening 80, which is provided in the form of a slot formed in the inner wall of the ring 261. It can be seen that a rim 81 formed on either side of the ring 261 is provided with a step 82 for receiving the respective hemispherical half 241 of the brush head 216. In this way, in particular as seen in FIG. 14, each half 241 of the head 216 forms an effective seal with the rim 81 of the ring 261, thereby preventing the ingress of water/toothpaste or other contaminants to the interior of the ring 261 where the belt 234 is housed. The ring 81 and step 82 also act as a bearing for each hemispherical half 241 of the head 216, allowing the head 216 to freely rotate when mounted to the ring 261. The two halves 241 of the head 216 are secured relative to one another by any suitable means, such that they will rotate in unison, thus effectively rendering the head 216 as a single sphere. The second pulley 263 is either sandwiched between the two halves of the head 216, or may be formed integrally with one or both of the hemispherical halves. As the belt 234 passes around the second pulley 263, it can then be used to drive the brush head 216.

Referring now to the first end 260, in particular as seen in FIG. 11, this is provided as an open ended cylinder having a mouth 83 from which partially projects a pair of drive gears 84 which are concentrically mounted on either side of the first pulley 262, and are fixed thereto. In this way rotation of one or other of the drive gears 84 will effect the simultaneous rotation of the first pulley 262. As the belt 234 is engaged around the first pulley 262, rotation of the drive gears 84 will effect the displacement of the belt 234 and therefore rotation of the head 216.

Referring now to FIG. 10 the system 210 again comprises a transducer 222, which is operable to impart the first and second independent motions to the head 216 via the coupling 214. The transducer 222 comprises an inlet or socket 272, which is dimensioned to slidingly receive, in a longitudinal direction, the first end 260 of the coupling 214 therein. The socket 272 and first end 260 are preferably provided with a key and corresponding keyway (not shown) in order to ensure the correct alignment between the coupling 214 and the transducer 222. Mounted to the transducer 222 and accessible through the socket 272, is a corresponding pair of drive gears 85 which, once the first end 260 is seated correctly within the socket 272, will mesh with the drive gears 84 projecting from the mouth 83 of the first end 260. The drive gears 85 are, in use, driven by a motor 212 provided as part of the toothbrush, which will thus effect, through the drive gears 84 and the belt 234, the first independent motion of the head 216.

Figure 10:
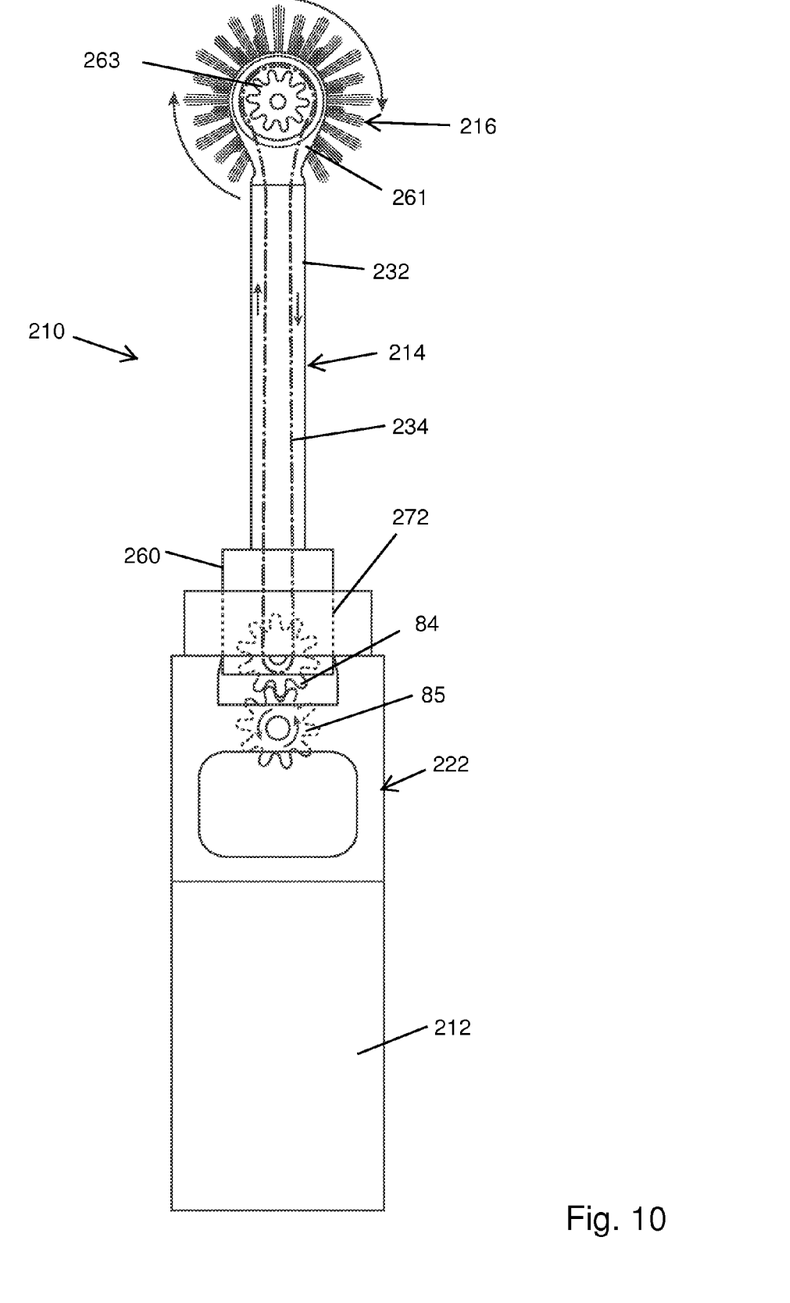
FIG. 10 illustrates a side elevation of an electric toothbrush according to a further alternative embodiment of the present invention.

The motor 212 is also adapted to effect the rotation of the entire transducer 222, which will effect the rotation of the coupling 214 about a longitudinal axis thereof, in order to effect the second independent motion of the brush head 216. It will be appreciated that these motions could be independently reversed, mixed, or programmed to occur in predetermined sequences, all through the transducer 222.

In use the transducer 222 will be housed within a body (not shown) of the toothbrush, and is preferably positioned such that the open end of the socket 272 is located coterminous with a free end of the body of the toothbrush, such as to permit the coupling 214 to be quickly and easily inserted and removed from the toothbrush. Once inserted into the socket 272, it is preferable that some form of locking means is engaged in order to prevent the accidental separation of the coupling 214 and transducer 222. Thus the coupling 214, carrying the brush head 216, can be quickly and easily pressed into or pulled out of engagement with the body of the electric toothbrush, in order to allow quick and easy user replacement. No portion of the body needs to be opened or closed in order to effect this replacement.

The drive system 10; 110; 210 may comprise, particularly when being used as part of an electric toothbrush, a guard (not shown) covering a potion of the head 16; 116; 216, for example in the form of a hemisphere surrounding half of the head. The guard (not shown) may be secured to the drive system 10; 110; 210 by any suitable means.

It will therefore be appreciated that the drive system 10; 110; 210 of the present invention allows two independent and/or simultaneous motions to be applied to a head such as a brush head 16; 116; 216 or the like with relatively simple components, and in an overall assembly which is relatively small in size to enable same to be used in a hand held and portable manner. The drive system 10; 110; 210 also enables the head 16; 116; 216 of the brush to be quickly and easily replaced by the end user. In addition the cost and complexity of manufacture of the system 10; 110; 210 will be relatively low in order to provide an economically viable product.

The invention claimed is:

1. A handheld device comprising:
   a drive system;
   a drive source for connection to the drive system; and
   a body housing the drive source;
   wherein the drive system comprises:
      a head; and
      a coupling connectable between the drive source and the head and operable to impart at least first and second independent rotary motions to the head and adapted to rotate the head about a first axis as the first motion and independently about a second axis as the second motion, the first and second axes being substantially orthogonal to one another, the coupling comprising a first pulley and a second pulley, and a belt extending between the first and second pulleys, the first pulley arranged to be driven by the drive source and the second pulley arranged to drive the head;
      wherein the drive system is releasably mountable to the body in operative engagement with the drive source such as to permit user replacement of the drive system.

2. A handheld device according to claim 1 in which the coupling is operable to impart continuous rotary motion to the head for both the first and the second motions.

3. A handheld device according to claim 1 in which the first and second axes pass through the centre of the head.

4. A handheld device according to claim 1 in which the coupling comprises an elongate rigid support extending between the first and second pulleys and at a free end of which support the head is mounted.

5. A handheld device according to claim 4 in which the belt extends substantially longitudinally of the support.

6. A handheld device according to claim 4 in which the support is rotatable by the drive source about a longitudinal axis of the support.

7. A handheld device according to claim 4 in which the support forms a guide for the belt.

8. A handheld device according to claim 4 in which the head comprises a rotatable element to which the coupling is arranged to impart the first and second independent motions.

9. A handheld device according to claim 8 in which the second pulley is formed integrally with the rotatable element.

10. A handheld device according to claim 8 in which the free end of the support comprises a tab having an aperture therein through which two halves of the rotatable element are secured to one another.

11. A handheld device according to claim 10 in which the tab comprises a ring and each half of the rotatable element forms a seal with the ring when secured thereto.

12. A handheld device according to claim 8 in which the head comprises an array of bristles extending outwardly from the rotatable element.

13. A handheld device according to claim 12 in which the bristles are provided on two halves of the rotatable element and are oriented, at or adjacent an interface between the halves, to converge in order to provide continuity to a cleaning surface defined by the bristles.

14. A handheld device according to claim 4, wherein the drive source comprises a pair of concentric drive shafts including a first shaft arranged to drive the first pulley and a second shaft arranged to effect rotation of the support.

15. A handheld device according to claim 14 in which the drive source comprises a clutch displaceable between an engaged state and a disengaged state, in the engaged state enabling synchronous rotation of the first and second shafts, and in the disengaged state enabling independent rotation of the first shaft.

16. A handheld device according to claim 4 comprising a sleeve surrounding at least a portion of the support and within which sleeve the support is rotatable about a longitudinal axis of the sleeve.

17. A handheld device according to claim 4 comprising a transducer disposed internally of the body and operable to transfer drive from the drive source to the first pulley and to effect rotation of the support relative to the body.

18. A handheld device according to claim 17 in which the transducer is rotatable within the body by the drive source in order to impart the second independent motion.

19. A handheld device according to claim 17, in which the drive system is insertable into the body and engagable with the transducer by means of the longitudinal insertion of a free end of the coupling into the body.

20. A handheld device according to claim 1 in which the belt comprises a toothed belt.

21. A handheld device according to claim 1 in which the coupling is releasably engagable with the drive source.

* * * * *